United States Patent

Basler et al.

(10) Patent No.: US 7,163,443 B2
(45) Date of Patent: Jan. 16, 2007

(54) METHOD, TOOL, AND MATCHING EQUIPMENT FOR PRODUCING DENTAL PROSTHETIC ITEMS

(75) Inventors: Franz Basler, Ketsch (DE); Joachim Pfeiffer, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 11/138,386

(22) Filed: May 27, 2005

(65) Prior Publication Data

US 2005/0266775 A1    Dec. 1, 2005

(30) Foreign Application Priority Data

Jun. 1, 2004    (DE)    ............... 10 2004 026 917

(51) Int. Cl.
*B24B 51/00*    (2006.01)
(52) U.S. Cl. ........................... 451/28; 451/5
(58) Field of Classification Search ............ 451/8–10, 451/21, 28, 5, 41, 56, 57; 125/11.02
See application file for complete search history.

(56) References Cited

U.S. PATENT DOCUMENTS 3,894,339 A    7/1975    Manzi
5,006,685 A *  4/1991    Hatano et al. ............. 219/69.2
5,200,591 A *  4/1993    Ooba ....................... 219/69.17
5,482,498 A *  1/1996    Higashikawa ............... 451/61
6,394,880 B1 * 5/2002    Basler et al. ................. 451/28

FOREIGN PATENT DOCUMENTS

BE    903012    12/1985
DE    4030176    3/1992

OTHER PUBLICATIONS

Abstract of BE 903012.

* cited by examiner

*Primary Examiner*—Lee D. Wilson
*Assistant Examiner*—Anthony Ojini
(74) *Attorney, Agent, or Firm*—Dykema Gossett PLLC

(57) ABSTRACT

A tool for use in machining equipment for machining a item from a workpiece via longitudinal and transverse movement includes stepped regions having different diameters, each provided with a lateral surface for transverse lateral machining and a front surface for longitudinal feed machining, the tool diameters in the stepped regions decreasing toward the forward face of the tool.

18 Claims, 2 Drawing Sheets

METHOD, TOOL, AND MATCHING EQUIPMENT FOR PRODUCING DENTAL PROSTHETIC ITEMS

BACKGROUND OF THE INVENTION

The invention relates to a method, tool, and machining equipment for the production of dental prosthetic items by means of transverse lateral machining and longitudinal feed machining.

For the production of dental prosthetic items, methods, machining equipment, and tools are known by means of which a blank is machined by milling and/or grinding.

DE 199 28 002 C1 describes a device and a method for the production of medical fittings. The grinding tools used therein have cylindrical lateral surfaces, and a cone apex having a point radius may be present.

DE 40 30 176 A1 describes a method of calibrating a motor-driven tool in machining equipment. The tool used in the machining equipment is a cylindrical pencil grinder.

TECHNICAL PROBLEM

The tools employed for the production of dental prosthetic items must be capable, for example, of making a dental crown exactly fit the geometry of the jaw or, in the case of dental prosthetic items, of minutely reproducing a complex tooth surface. To this end, on the one hand, a great deal of material has to be removed from a blank, but, on the other hand, it may happen that narrow recesses have to be carved. For this reason, tools are often used which have a comparatively pointed shape, eg that of a long cone. Such machining tools, however, have a number of disadvantages. One such drawback is that the machining equipment, in order to achieve high precision, must be calibrated at regular intervals. The machining tools are subject to normal wear and tear and the exact shape of the tool must additionally be included in the calibration. Particularly in the case of machining tools having only oblique contours, exact measurement of the tool proves to be very difficult.

Moreover, when machining workpieces and a long-cone-shaped tool is not rested against the workpiece at right angles thereto, additional forces are caused to be applied to the tool, and these have to be taken into consideration in the construction of such a tool and usually have to be compensated for by greater material strengths. When these thicker tools are used, however, it is no longer possible to carve all recesses. Furthermore, in certain situations the inclined surface to be machined regularly causes the tool to "float off", that is to say, an elastic deformation of the tool is caused as a result of one-sided loading, which leads to deviation from the planned machining path and thus causes reduced machining accuracy.

In addition, it is known that when excavating recesses in brittle materials tools of long conical shape, such as are usually used in the production of dental prosthetic items, can cause break-off of the material.

It is thus an object of the present invention to overcome the above-mentioned drawbacks involved in the machining of dental prosthetic items using tools of this type by providing a method, machining equipment, and a tool enabling very precise machining with a minimum frequency of tool changes and long lifetimes of the tools employed.

DISCLOSURE OF THE INVENTION

According to the invention, dental prosthetic items are machined in machining equipment using a method which employs a tool for transverse lateral machining and longitudinal feed machining. The tool possesses a stepped arrangement of regions having different diameters, each region possessing a lateral surface for transverse lateral machining and a front surface for longitudinal feed machining, whilst the diameters of said regions decrease toward the forward face of the tool.

Using this method, with which it is possible to carry out machining in a direction perpendicular to the tool axis as well as in the longitudinal direction of the tool axis, sufficiently fine structures can be carved on account of the slender tool point, whilst on the other hand large amounts of material can be removed and the tool is more accurately guided, all of which leads to more rapid machining and enhanced precision.

Advantageously, machining is substantially carried out by grinding the blank. It is thereby possible to machine even high-strength materials, such as are often employed in dentistry.

Advantageously, the diameter of the tool used is constant in each of the stepped regions. On the one hand, this facilitates scanning of the tool for the purpose of determining the degree of wear and the position of the contour of the tool whilst avoiding, on the other hand, the aforementioned drawbacks which frequently arise when using tools with slanting machining surfaces.

Advantageously, the diameters of the stepped regions decrease toward the forward face of the tool so that the envelope of the tool describes a cone which has an aperture angle of from 4 to 20 degrees. It is thus possible to carve even narrow recesses.

A particularly advantageous further development of the method relates to the use of a tool which has a coating containing abrasive particles. The tool can thus be optimized with respect to its functionality and durability. Coatings of this type have long been part of the prior art and are efficient.

Advantageously, the nature of the coating is different in the various regions of the tool. Thus there can be regions in which, for example, a coarse coating is present for high removal of material whilst in other regions there can be a fine coating for precision machining of the dental prosthetic item. It is particularly advantageous if the particle size is of different coarseness in the various regions. In this way, the advantageous division between coarse and less coarse grinding regions, as described above, can be achieved. Moreover, the layer thickness of the coating can also be adjusted to the wear to be expected during machining by providing a greater layer thickness in regions of increased wear.

Advantageously, the method can be carried out at least until the coating of the tool has worn down to half or less of the original thickness. On the one hand, this will afford a constant material machining effect and, on the other hand, a long life of the tool. The wear can be corrected by calibration of the machining equipment.

This makes possible long service lives and economical use of the tool used for carrying out the method.

The invention further relates to a tool and to machining equipment for carrying out the method.

The tool has regions which are arranged in steps and have different diameters, each region possessing a lateral surface for transverse lateral machining and a front surface for longitudinal feed machining, the diameters of these stepped regions decreasing toward the forward face of the tool.

Preferably, the diameter of the tool within each of said regions is constant and the respective diameters decrease toward the forward face of the tool such that its envelope describes a cone which has an aperture angle of from 4 to 20 degrees.

Advantageously, the tool has a transition region extending from the front lateral surface having a first radius to the forward face of the tool having a second radius which is smaller than said first radius, which transition region defines a predefined surface, which has a curvature having a third radius likewise smaller than said first radius.

With this geometry of the surface of the transition region it is possible, for example, to reduce the tendency of the tool to slip off on a slanting surface. Ideally, the third radius should be as small as possible, since the area of the surface having a transverse component, which produces a lateral force during longitudinal feed of the tool, would then be particularly small. However, technical limits are placed on the producibility of the tool so that instead of a sharp edge there will be obtained, in practice, a slightly rounded edge. However, even if a sharp edge could be formed, it would not remain sharp, but would be broken, on account of wear, long before the actual lifetime of the tool is reached.

Instead of a plane forward face, other shapes may be produced, if desired. A particular example thereof is a spherical or lenticular forward face instead of a flat forward face showing a transition region toward the lateral surface. The transition region extending from one radial lateral surface to the adjacent radial lateral surface is preferably in the form of a horizontal surface, which can be regarded as an annular plane front face. Here again, other shapes may be provided, if desired.

An advantageous embodiment consists in the provision of a forward face in the form of an apex having an aperture angle of from 30° to 60°, in particular 45°. The apex is thus confined within the envelope. With a point of this type, the carving of fine structures, such as fissures, on the tooth is possible without inducing tool float-off to any significant extent.

A particularly advantageous further development of the method relates to the use of a tool which has a coating. The tool can thus be optimized with respect to its functionality and durability.

Advantageously, the nature of the coating differs in the various regions of the tool. Thus there can be regions in which, for example, a coarse coating is present for high removal of material, whilst in other regions a fine coating may be present for precision machining of the dental prosthetic item. Moreover, it is advantageous when the layer thickness of the coating is greater in the region of the point of the tool, since this region is subject to the greatest amount of wear.

For use as a grinding tool, it has proven to be advantageous to provide the coating with abrasive particles.

Coatings of this type have long been part of the prior art and are cost-effective and efficient.

It is particularly advantageous if the particle size in the various regions is of different coarseness. The advantageous division between coarse and less coarse grinding regions described above can thus be achieved.

Advantageously, the coating can be worn down to at least half of the original thickness during machining. The wear can be corrected by calibration of the machining equipment. This is conducive to long service lives and economical use of the tool used for carrying out the method.

The machining equipment for carrying out the method using this tool has control means adapted to the tool and to the method.

BRIEF DESCRIPTION OF THE DRAWINGS

The method according to the invention is illustrated with reference to the drawings, in which.

DETAILED DESCRIPTION OF PREFERRED EMBODIMENTS

Figure 1:
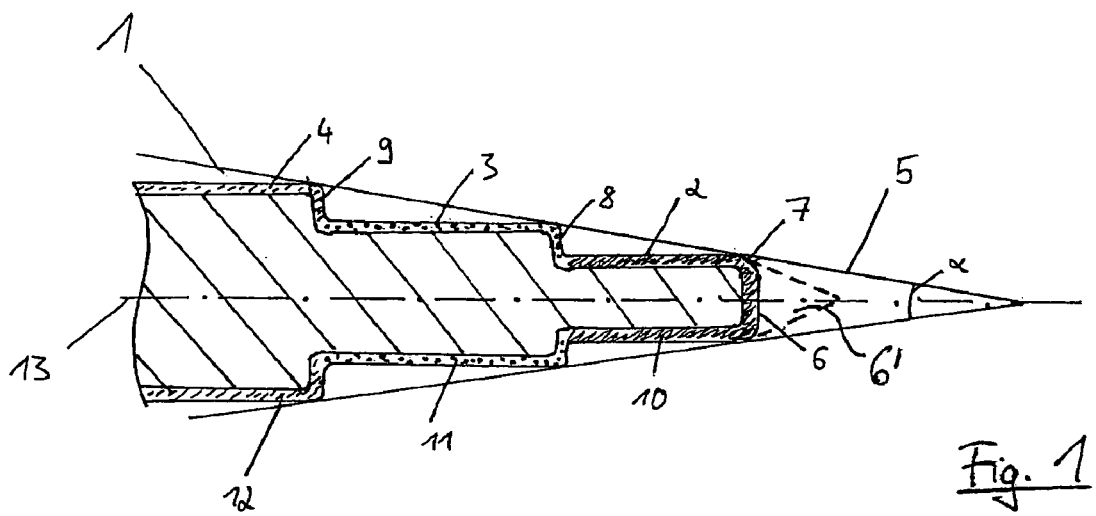
FIG. 1 shows a cross-section of a tool for carrying out the method according to the invention.
Figure 3:
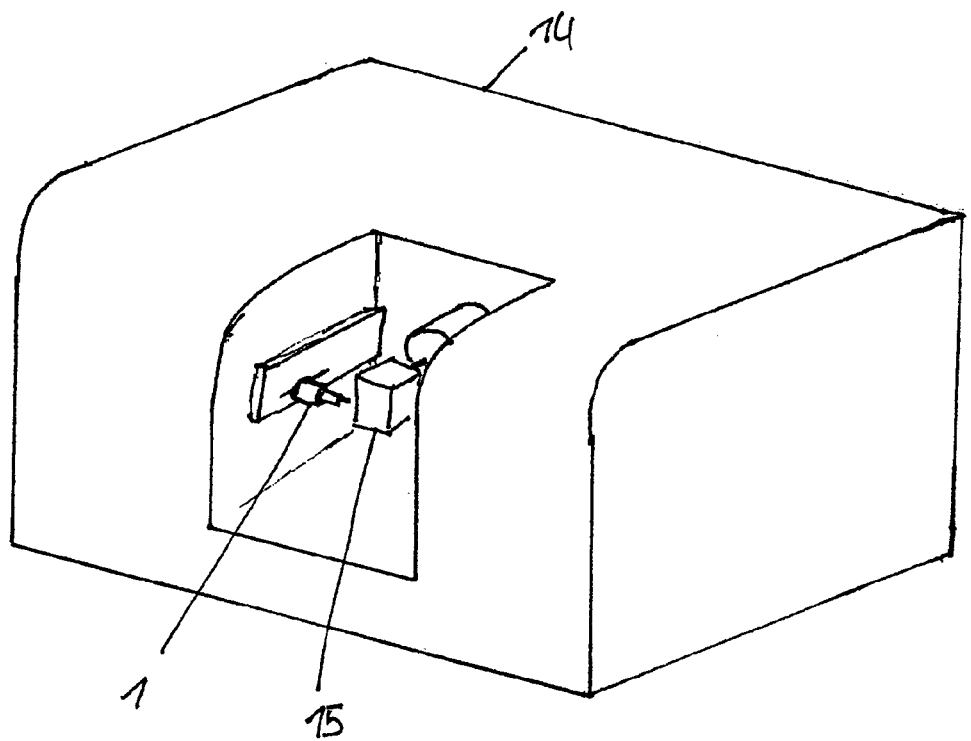
FIG. 3 shows machining equipment which employs a tool as shown in FIG. 1.

FIG. 1 shows a cross-section through an axially symmetrical tool 1 for carrying out the method according to a preferred embodiment of the invention using machining equipment according to the invention as represented in FIG. 3. For transverse lateral machining by grinding, a number of cylindrical lateral surfaces 2, 3, 4 are provided whose lengths and respective radius differences are related to one another such that their edges form a conical envelope 5 having an angle $\alpha$ of, in this case, 18°, for example. Most frequently, cylindrical grinders having a cone angle of, say, 4° are used; the relatively large cone angle shown here serves primarily for better illustration thereof.

The point of tool 1 is provided with a forward face 6. The transition region extending from said forward face 6 to the first lateral surface 2 has a defined form 7 which, regarded in cross-section, represents the arc of a circle.

Furthermore, an alternative embodiment having an apex 6' is shown in dashed lines, this having an aperture angle of from 30° to 60°, here 45°, so that it is enclosed by the envelope 5.

In the transition regions of the cylindrical lateral surfaces 2, 3, 4, further front surfaces 8, 9 are provided, the transition regions between these being similar to the contour of transition region 7. These other front surfaces 8, 9 are in the form of annular surfaces and are disposed symmetrically about a center axis 13 of tool 1.

The surface of the tool 1 consists of various coatings 10, 11, 12, which can be applied to the raw material of the tool by known methods. The coatings 10, 11, 12 contain abrasive particles having different particle sizes, the coarseness of which increases with increasing tool diameter. Thus coating 10 is suitable for fine finishing and for carving fine contours, whereas coating 12 achieves higher removal of material. It is particularly advantageous to use an apex 6' in such a case.

The use of a tool of this type is recommended if the machining strategy for the production of a dental prosthesis from a blank is divided specifically into transverse lateral machining and longitudinal feed machining. This makes it possible for the tool to always exert only a perpendicular force on the workpiece, which on the one hand reduces the loads acting on the tool and on the other hand prevents tool float-off and thus increases product precision.

Figure 2:
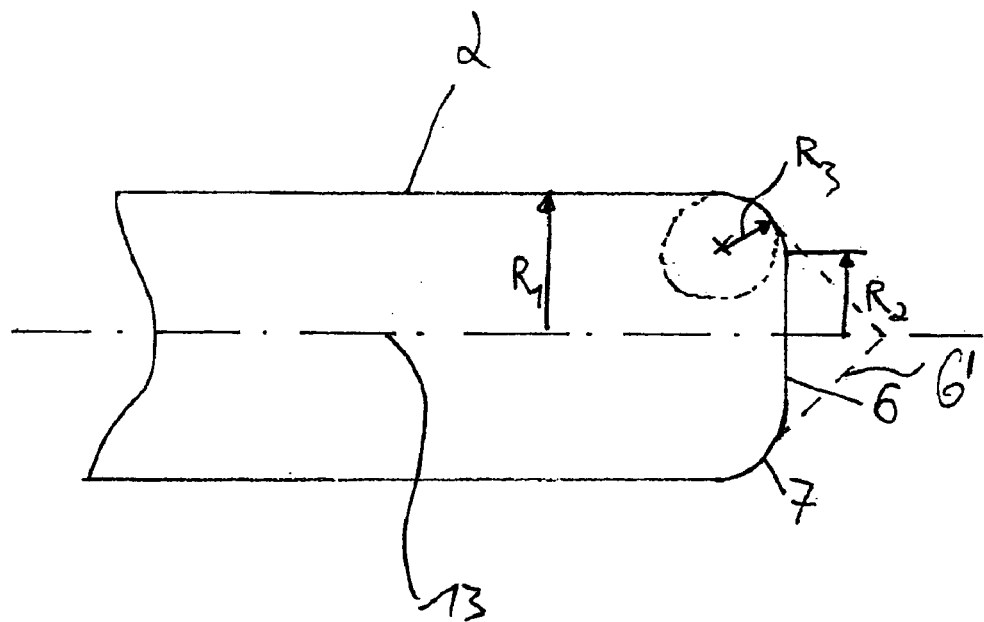
FIG. 2 shows part of the cross-section of FIG. 1 in the region of the forward face of the tool.

FIG. 2 shows part of FIG. 1 in order to illustrate more accurately the geometrical relationships operating in the transition region between the forward face 6 and the first lateral surface 2. As measured from center axis 13, the lateral surface 2 lies on a radius $R_1$ and the forward face 6 extends over a radius $R_2$ such that it is in the form of a circular plane region.

The transition region 7 has a curvature having a radius $R_3$, which is calculated such that tangential adjoinments to forward face 6 and first lateral region 2 result. This is not absolutely necessary and radius $R_3$ may be dimensioned such that no tangential adjoinment of the transition region 7 results, but rather an edge is formed which may also have a radius of curvature.

FIG. 3 shows machining equipment 14 as proposed by the invention. A tool 1 and a workpiece 15 are mounted for mutual displaceability such that the desired contour can be carved from workpiece 15 using tool 1.

Figure 4:
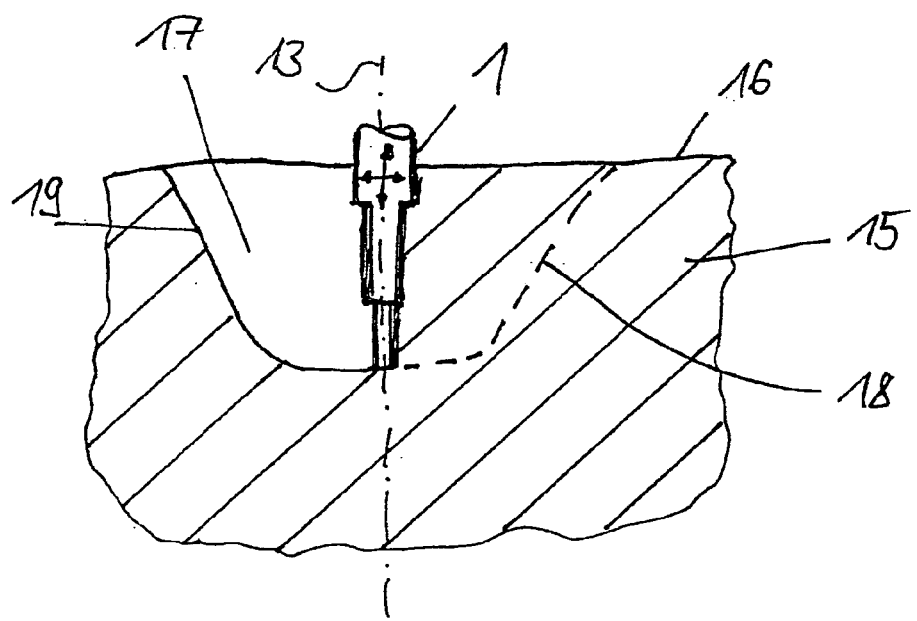
FIG. 4 shows a tool when machining of a workpiece is in progress.

FIG. 4 is a detail showing tool 1 while machining of workpiece 15 is in progress. On account of the outer surfaces being disposed substantially only radially and at right angles to the longitudinal axis 13 of the tool, machining of workpiece 15 can be simply broken down into the components transverse lateral machining and longitudinal feed machining. If the tool is moved according to these components, there will be an approximate alignment of tool feed and action of force. This alignment is not afforded, for example, in the case of a conical grinder on account of its lateral surface showing simultaneously longitudinal and transverse components, which leads to the disadvantageous effects already described beforehand, in particular to tool float-off.

However, it is also possible, using component-wise breakdown, to effect control of the tool such that it is simultaneously fed in the longitudinal direction and in the transverse direction so that a combined longitudinal/transverse feed of the tool takes place. This is easy to achieve if the feed takes place in an order of magnitude which lies within the dimensions of the cutting edges, i.e. in the case of a coating containing abrasive particles which project, for example, 60 μm from the base material of the coating, the feed can be 10 μm, that is only a sixth part thereof. It will be readily appreciated that this feed rate can be realized under conditions of this kind without causing any significantly adverse effects on the accuracy of machining. When using a coating whose abrasive particles project by only 10 μm, however, the feed will, of course, have to be reduced.

Furthermore, the tool can be controlled such that the feed for the next machining step takes place exclusively as a longitudinal feed if this is greater than the intended transverse feed.

The machining strategy here is such that the proportion of transverse lateral machining is maximized, since significantly more grinding material is present on the cylindrical lateral surfaces 2, 3, 4 than on the comparatively small front surfaces 6, 8, 9 (FIG. 1).

During machining, the tool 1 first enters the workpiece 15 with its forward face 6. Depending on the machining depth, the other front faces 8, 9 (FIG. 1) will also come into contact with workpiece 15. On reaching the necessary depth, tool 1 then carves a recess 17 along the desired contour 18 laterally using the lateral surfaces 2, 3, 4 (FIG. 1) without the front faces 6, 8, 9 (FIG. 1) coming into action. The opposite flanks of such a recess 17 can at most have the same angle α of the envelope of the tool, due to the shape of the tool.

Since in the regions near the surface 16 of workpiece 15 more material must be removed in the same period of time than in the deeper-lying regions, a coating which becomes coarser with increasing distance from the forward face 6 is advantageous, since it will then be possible to advance tool 1 more rapidly.

The coatings 10–12 on the lateral surfaces 2–4 shown in FIG. 1 are designed such that coarse machining takes place when using the lateral surfaces 3, 4, whereas fine machining takes place when using the lateral surface 2. In order to compensate for relatively high wear of coating 10 on lateral surface 2 in the region of the point of the tool during fine machining, coating 10 can have a greater thickness than coatings 11, 12 and for this purpose can be in the form of, say, a double layer or a multiple layer. This also applies, of course, to the coating on the forward faces 6, 8, or 9 or on the transition region 7 and also on the corresponding transition regions between forward faces 8, 9 and lateral surfaces 3, 4.

LIST OF REFERENCE NUMERALS 1 tool
2, 3, 4 regions, lateral surface
5 envelope
6 forward face
6' cone apex
7 transition region
8, 9 front surface
10, 11, 12 coating
13 center axis
14 machining equipment
15 workpiece
16 surface of workpiece
17 recess
18 contour to be excavated
19 flank

The invention claimed is:

1. A method of machining a workpiece to produce a dental prosthetic item comprising providing a tool for transverse lateral machining and longitudinal feed machining, said tool having stepped regions with different diameters, each stepped region comprising a lateral surface for transverse lateral machining and a front surface for longitudinal feed machining, the diameters of said stepped regions being dimensioned so as to decrease toward a forward face of said tool, and moving said tool against and into a workpiece to form said dental prosthetic item.

2. A method as defined in claim 1, wherein said tool is rotated to grind said workpiece.

3. A method as defined in claim 2, wherein the tool includes a coating containing abrasive particles, the particle size of said abrasive particles in said coating being different in at least two different regions.

4. A method as defined in claim 1, wherein the diameter of each said stepped region is constant.

5. A method as defined in claim 1, wherein the diameters of said stepped regions decrease toward a forward face such that an envelope defined thereby forms a cone having an aperture angle (α) of between 4 and 20 degrees.

6. A method as defined in claim 5, wherein precision machining is carried out at a tip of the tool simultaneously by said forward face and the adjacent lateral surface and coarse machining is carried out by a front surface spaced at a distance from said tool tip and/or by a lateral surface.

7. A tool for the production of a dental prosthetic item by transverse and longitudinal machining, of a workpiece, said tool comprising stepped regions having different diameters, each stepped region defining a lateral surface for transverse lateral machining and a front surface for longitudinal machining, diameters of said stepped regions being dimensioned so as to decrease toward a forward face of said tool.

8. A tool as defined in claim 7, wherein the diameter of each of the stepped regions is constant.

9. A tool as defined in claim 7, wherein the diameters in the stepped regions decrease toward said forward face such that an envelope defined thereby forms a cone having an aperture angle ($\alpha$) of from 4 to 20 degrees.

10. A tool as defined in claim 7, wherein a transition region between the forward lateral surface having a first radius and said forward face having a second radius smaller than said first radius is designed such that it forms a curvature having a third radius which is also smaller than said first radius.

11. A tool as defined in claim 7, wherein at said forward face there is a conical point which has a cone angle of from 30° to 60°.

12. A tool as defined in claim 11, wherein said cone angle is 45°.

13. A tool as defined in claim 7, wherein said tool has a coating.

14. A tool has defined in claim 13, wherein the nature of said coating is different in each of the stepped regions.

15. A tool as defined in claim 13, wherein said coating contains abrasive particles.

16. A tool as defined in claim 15, wherein the particle size of said coating is different in each of the stepped regions.

17. A tool (1) as defined in claim 15, wherein a layer thickness of said coating is greater in the region at a tip of said tool.

18. Machining equipment for producing dental prosthetic items, comprising a tool for transverse lateral machining and longitudinal feed machining as defined in claim 7.

* * * * *